(12) United States Patent
Telang

(10) Patent No.: US 12,201,792 B2
(45) Date of Patent: Jan. 21, 2025

(54) METHOD FOR MAKING A GUIDEWIRE FROM A DRAWN-FILLED TUBE OF A STAINLESS STEEL SHEATH JACKETING A NITINOL CORE WIRE

(71) Applicant: Lake Region Manufacturing, Inc., Chaska, MN (US)

(72) Inventor: Abhishek M. Telang, Minneapolis, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 700 days.

(21) Appl. No.: 17/412,480

(22) Filed: Aug. 26, 2021

(65) Prior Publication Data

US 2021/0379341 A1  Dec. 9, 2021

Related U.S. Application Data

(62) Division of application No. 15/964,112, filed on Apr. 27, 2018, now Pat. No. 11,426,560.

(60) Provisional application No. 62/490,807, filed on Apr. 27, 2017.

(51) Int. Cl.
A61M 25/09    (2006.01)

(52) U.S. Cl.
CPC ........... *A61M 25/09* (2013.01); *A61M 2025/09091* (2013.01); *A61M 2025/09108* (2013.01); *A61M 2025/09133* (2013.01); *A61M 2025/09166* (2013.01); *A61M 2025/09175* (2013.01); *A61M 2205/0266* (2013.01)

(58) Field of Classification Search
CPC ........ A61M 25/09; A61M 2025/09091; A61M 2025/09108; A61M 2025/09133; A61M 2025/09166; A61M 2025/09175; A61M 2205/0266

See application file for complete search history.

(56) References Cited

U.S. PATENT DOCUMENTS

| | | | | |
|---|---|---|---|---|
| 4,796,642 A | * | 1/1989 | Harris | A61N 1/056 600/585 |
| 4,991,602 A | * | 2/1991 | Amplatz | A61M 25/09 604/528 |
| 5,308,324 A | | 5/1994 | Hammerslag et al. | |
| 5,507,729 A | * | 4/1996 | Lindenberg | A61M 25/09 604/170.01 |
| 5,640,970 A | | 6/1997 | Arenas | |
| 5,664,580 A | * | 9/1997 | Erickson | A61M 25/09 128/877 |

(Continued)

OTHER PUBLICATIONS

"Extended European Search Report", Application 18169980.2, dated Sep. 28, 2018.

*Primary Examiner* — Rene T Towa
*Assistant Examiner* — Justin Xu
(74) *Attorney, Agent, or Firm* — Michael F. Scalise

(57) ABSTRACT

A guidewire made from a drawn-filled tube composite wire is described. The composite wire has a stainless steel outer sheath jacketing a nitinol core wire. The drawn-filled tube composite wire is ground at its distal end to expose the nitinol core, which has superelastic and kink resistant properties that are desirable for the distal end of a guidewire. The proximal end of the drawn-filled tube is not ground or if ground, the outer sheath of stainless steel is not removed to an extent sufficient to expose the nitinol core.

23 Claims, 4 Drawing Sheets

(56) References Cited

U.S. PATENT DOCUMENTS

| | | | | |
|---|---|---|---|---|
| 6,019,668 | A * | 2/2000 | Ramanath | B24D 5/06 |
| | | | | 451/542 |
| 6,142,975 | A | 11/2000 | Richardson et al. | |
| 6,165,140 | A | 12/2000 | Ferrera | |
| 6,694,595 | B1 | 2/2004 | Anderson et al. | |
| 6,884,225 | B2 | 4/2005 | Kato et al. | |
| 7,015,392 | B1 | 3/2006 | Dickenson | |
| 7,322,944 | B2 * | 1/2008 | Osawa | A61M 25/09 |
| | | | | 600/585 |
| 7,645,242 | B1 | 1/2010 | Jalisi et al. | |
| 7,989,703 | B2 | 8/2011 | Schaffer et al. | |
| 7,998,090 | B2 | 8/2011 | Cornish et al. | |
| 8,500,658 | B2 | 8/2013 | Purtzer et al. | |
| 8,569,625 | B2 | 10/2013 | Slininger et al. | |
| 8,835,799 | B2 | 9/2014 | Slininger et al. | |
| 9,033,004 | B2 | 5/2015 | Mishima et al. | |
| 9,061,088 | B2 | 6/2015 | Simpson | |
| 9,526,454 | B2 * | 12/2016 | Mellin | A61B 5/0215 |
| 10,179,225 | B2 * | 1/2019 | Sos | A61M 25/09041 |
| 11,400,261 | B2 * | 8/2022 | Mathews | A61F 2/2436 |
| 2005/0027214 | A1 | 2/2005 | Murayama et al. | |
| 2006/0074403 | A1 * | 4/2006 | Rafiee | A61M 25/0041 |
| | | | | 604/530 |
| 2009/0131913 | A1 | 5/2009 | Grandfield et al. | |
| 2009/0275862 | A1 | 11/2009 | Elsesser | |
| 2012/0041342 | A1 | 2/2012 | Purtzer | |
| 2012/0245488 | A1 * | 9/2012 | Matsumoto | A61M 25/09 |
| | | | | 600/585 |
| 2013/0304108 | A1 | 11/2013 | Weber et al. | |
| 2015/0173794 | A1 * | 6/2015 | Kurth | A61B 17/0057 |
| | | | | 600/203 |
| 2015/0314109 | A1 | 11/2015 | Minar et al. | |
| 2016/0279391 | A1 | 9/2016 | Gupta et al. | |

\* cited by examiner

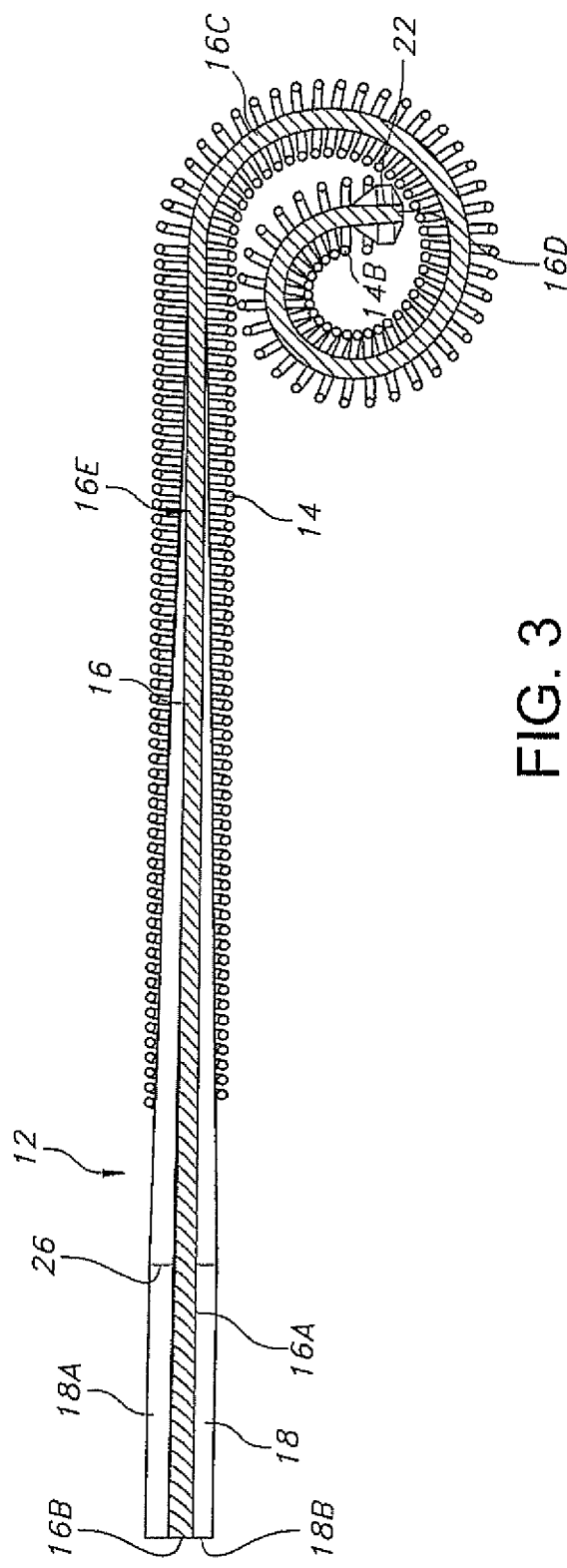
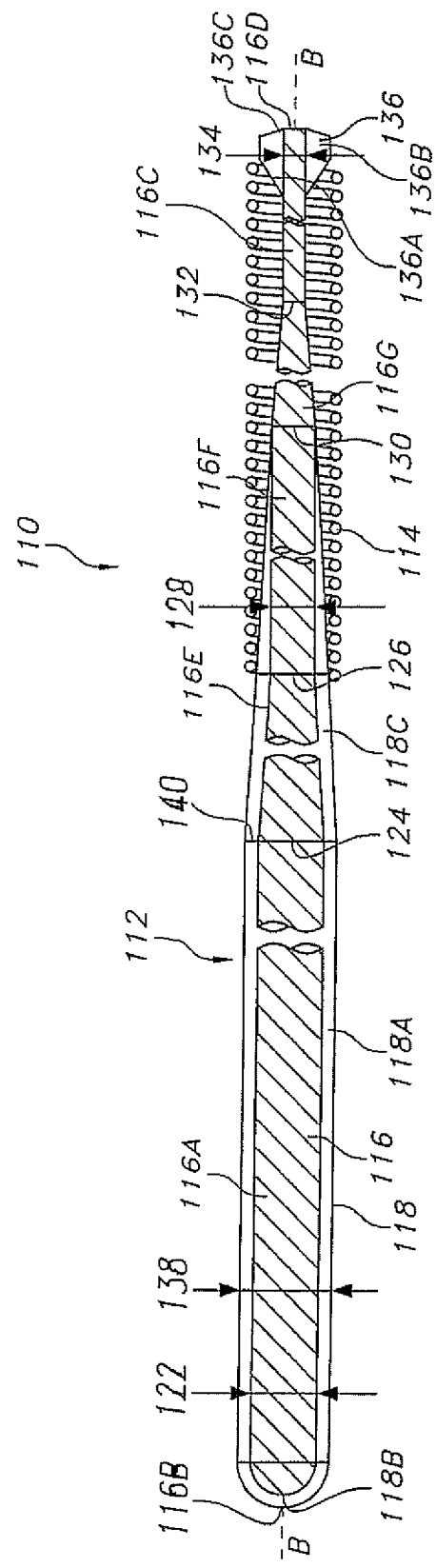
FIG. 3
FIG. 4A

METHOD FOR MAKING A GUIDEWIRE FROM A DRAWN-FILLED TUBE OF A STAINLESS STEEL SHEATH JACKETING A NITINOL CORE WIRE

CROSS-REFERENCE TO RELATED APPLICATIONS

This application is a divisional of U.S. patent application Ser. No. 15/964,112, filed on Apr. 27, 2018, now U.S. Pat. No. 11,426,560, which claims priority to U.S. provisional application Ser. No. 62/490,807, filed on Apr. 27, 2017.

BACKGROUND OF THE INVENTION

The present invention generally relates to the field of guidewires. More particularly, the present invention relates to various embodiments of guidewires that are useful for advancing intraluminal devices such as stent delivery catheters, balloon dilatation catheters, atherectomy catheters, and the like, through a patient's body, such as through a patient's vasculature. This invention is also useful for electrophysiology catheters.

SUMMARY OF THE OF INVENTION

The present invention relates to a guidewire that is specifically designed for use in various minimally invasive vascular applications. Its foundation is a composite drawn-filled tube that is constructed of a stainless steel sheath jacketing a nitinol core wire. The distal portion of the drawn-filled tube is machined to remove the stainless steel sheath and expose the nitinol core wire. The distal end of the nitinol wire is the end which interacts with the patient and must be atraumatic, kink resistant, and flexible. However, nitinol is a super-elastic material providing good kink-resistance, but lacking pushability due to an inherently lower Young's modulus resulting in less support in delivering therapy or devices. A portion of the stainless steel sheath is left at the very distal end of the drawn-filled tube to provide an atraumatic tip. Immediately proximal the tip, the bared nitinol can be heat treated, flattened in a cold work process, or shape-set to provide kink resistance and a desired degree of flexibility.

The proximal portion of the drawn-filled tube is not machined, leaving stainless steel jacketing the nitinol core wire. Owing to its high yield strength and Young's modulus, stainless steel provides the guidewire with goad pushability and torque transmission. Pushability and torque transmission are important to the proper functioning of a guidewire when navigating to a desired vascular site to deliver the intended diagnosis or therapeutic treatment.

These and other aspects of the present invention will become more apparent to those of ordinary skill in the art by reference to the following detailed description and the appended drawings.

BRIEF DESCRIPTION OF THE DRAWINGS

In the drawings, like reference numbers generally refer to the same parts throughout the different views. Also, the drawings are not necessarily to scale, emphasis instead being generally placed upon illustrating the principles of the present inventions.

FIG. 3 is a side elevational view of the guidewire 10 shown in FIG. 1 with the distal portion 16D of the nitinol core wire 16 having been shape-set into a desired configuration.

FIG. 4A is an elevational view of a second embodiment of an exemplary guidewire 110 according to the present invention.

DETAILED DESCRIPTION OF THE PREFERRED EMBODIMENTS

Figure 1:
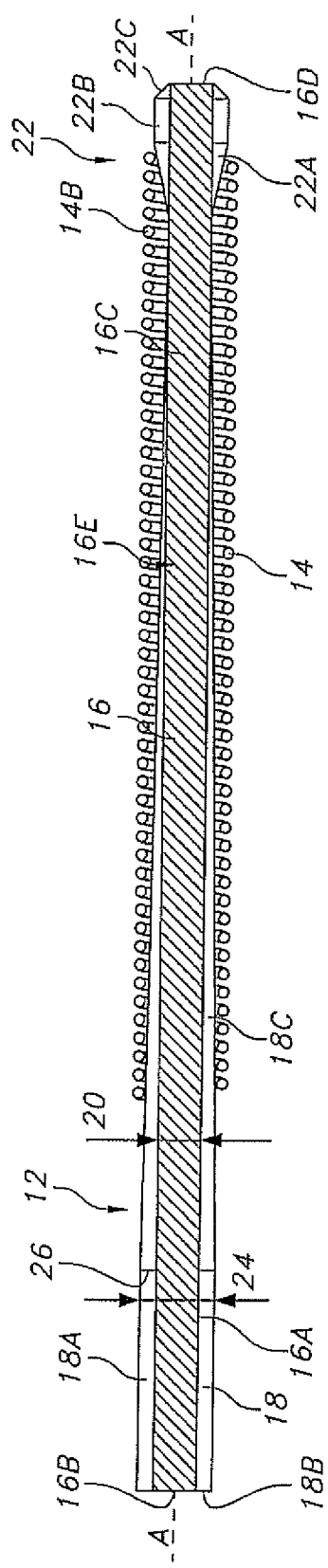
FIG. 1 is an elevational view of a first embodiment of an exemplary guidewire 10 comprising a drawn-filled tube 12 as a composite of a core wire 16 and a jacketing outer sheath 18 supporting a coil spring 14 according to the present invention.

Turning now to the drawings, FIG. 1 is an elevational view of one exemplary embodiment of a guidewire 10 according to the present invention. The guidewire 10 is comprised of a machined composite drawn-filled tube 12 supporting a helical or coil spring 14. The drawn-filled tube 12 has an inner core wire 16 surrounded or jacketed by an outer sheath 18. The core wire 16 is preferably made of nitinol being a superelastic nickel-titanium alloy wire comprising, for example, a composition in the range of from about 54 atomic % nickel:about 46 atomic % titanium to about 57 atomic % nickel:about 43 atomic % titanium. The outer sheath 18 is preferably made of stainless steel, for example 304 stainless steel. The coil spring 14 is also made of stainless steel, preferably 304 stainless steel. The guidewire 10 has a length ranging from about 50 cm to about 350 cm.

The core wire 16 extends along a longitudinal axis A-A from a core wire proximal portion 16A having a proximal end 16B to a core wire distal portion 16C having a distal end 16D. In this exemplary embodiment, the inner core wire 16 has a substantially constant diameter 20 ranging from about 0.004" to about 0.030" extending from the core wire proximal end 163 to the distal end 16D. An atraumatic distal tip 22 is provided at the core wire distal end 16D. The atraumatic tip 22 is made of stainless steel, preferably 304 stainless steel.

The outer sheath 18 is comprised of an outer sheath proximal portion 18A having a proximal end 18B. The outer sheath has a substantially constant thickness of from about 0.002" to about 0.008" so that the outer diameter 24 of the outer sheath jacketing the inner core wire ranges from about 0.008" to about 0.038" extending along the length of the proximal portion 18A. At the cross-section indicated at 26, the outer sheath 18 transitions to a tapered portion 18C that gradually reduced in cross-sectional diameter as it extends distally and downwardly toward the longitudinal axis A-A and the outer surface 16E of the inner core wire 16. The outer sheath 18 terminates or tapers out at the outer surface 16E of the core wire 16 at a location that is proximal the atraumatic tip 22.

The atraumatic tip can be a separate member that is secured to the core wire 16 at its distal end 16D or, preferably, the tip 22 is a portion of the outer sheath 18 supported on the core wire 16. The atraumatic tip has a beveled surface 22A that widens in cross-section from the core wire 16 to an intermediate cylindrical portion 22B. A sloped portion 22C extends distally and downwardly from the intermediate cylindrical portion 22B toward the core wire distal end 16D. If desired, the sloped portion 22C can be curved to further enhance the atraumatic shape of the tip 22. The intermediate cylindrical portion 22B of the tip 22 comprising the outer sheath 18 jacketing the inner core wire 16 has an outer diameter that is substantially the same as the outer diameter 24 of the outer sheath proximal portion 18A ranging from about 0.008" to about 0.038".

The proximal end 14A of the coil spring 14 is connected to the tapered portion 18C of the outer sheath 18. This connection is distal the outer sheath proximal portion 18A having the substantially constant outer diameter 24. The opposite distal end 14B of the coil spring 14 is connected to the atraumatic tip 22, preferably to its beveled surface 22A. The connections of the coil spring proximal end 14A to the tapered portion 18C of the outer sheath 18 and of the coil spring distal end 14B to the beveled portion 22A of the atraumatic tip 22 are made as a laser welder, a braze, or using a solder, and the like.

Figure 2:
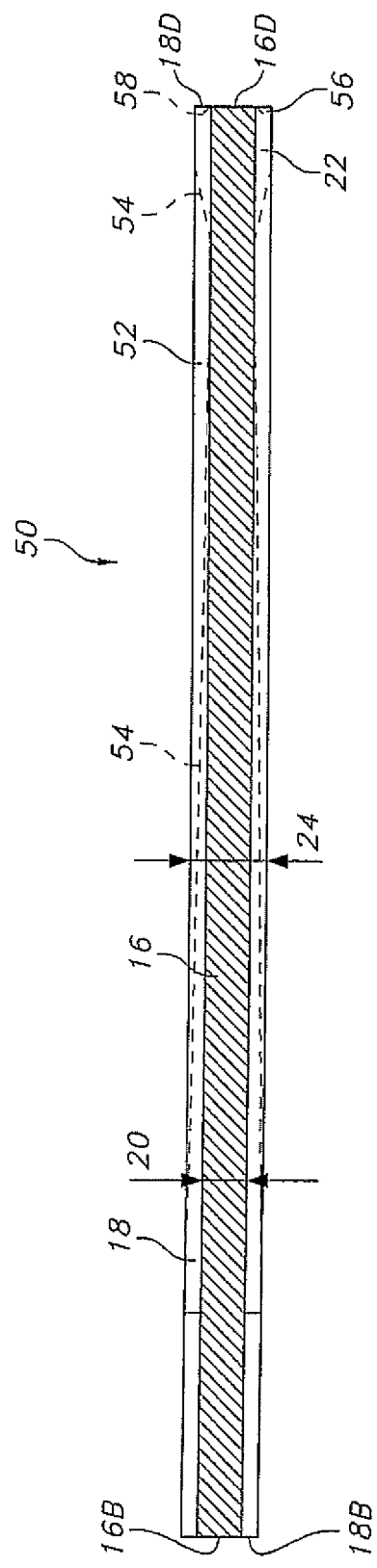
FIG. 2 is an elevational view of an exemplary drawn-filled tube 50 that shows in dashed lines 54 and 58 that selected portions of the outer stainless steal sheath 18 have been removed through a machining process to expose the nitinol core wire 16 to thereby provide the machined drawn-filled tube 12 illustrated in FIG. 1.

FIG. 2 illustrates a drawn-filled tube 50 that is useful for manufacturing the guidewire 10 shown in FIG. 1. The drawn-filled tube 50 is a composite of the core wire 16 jacketed by the outer sheath 18. The core wire 16 has the substantially constant diameter 20 ranging from about 0.004" to about 0.030" extending from the core wire proximal end 16B to the core wire distal end 16D. The outer sheath 18 has the substantially constant thickness ranging from about 0.002" to about 0.008". That way, the outer diameter 24 of the outer sheath 18 jacketing the inner core wire ranges from about 0.008" to about 0.038" extending from the outer sheath proximal end 18B to an outer sheath distal end 18D. The drawn-filled tube 50 is then subjected to a manufacturing process, for example a cam grinding process to remove the major portion 52 of the outer sheath 18 indicated by dashed lines 54 and the minor portion 56 indicated by the dashed lines 58. The resulting machined drawn-filled tube 12 comprising the outer sheath 18 jacketing the core wire 16 has the structure shown in FIG. 1. It is noted that the material of the outer sheath 18 bounded by dashed lines 54 and 58 forms the atraumatic tip 22.

FIG. 3 illustrates the guidewire 10 shown in FIG. 1, but with the distal portion 16C of the core wire 16 having been shape-set into a desired curved configuration. Shape setting the nitinol distal portion 16C or modifying the nitinol super-elastic properties locally is done in an annealing step where the nitinol is heated to a temperature of from about 300° C. to about 600° C. for a period of time ranging from about five minutes to about two hours. This annealing step is preferably performed prior to connecting the coil spring 14 to the machined drawn-filled tube 12. Alternately, the coil spring 14 is attached to the machined drawn-filled tube 12 prior to the annealing step. The guidewire 110 has a length ranging from about 50 cm to about 350 cm.

FIG. 4A shows a second embodiment of an exemplary guidewire 110 according to the present invention. The guidewire 110 is comprised of a composite drawn-filled tube 112 supporting a helical or coil spring 114. As is the case with the guidewire 10 illustrated in FIGS. 1 and 2, the drawn-filled tube 112 is comprised of a core wire 116 surrounded or jacketed by an outer sheath 118. The core wire 116 is preferably made of nitinol being a superelastic nickel-titanium alloy wire comprising, for example, a composition in the range of from about 54 atomic % nickel:about 46 atomic % titanium to about 57 atomic % nickel:about 43 atomic % titanium. The outer sheath 118 and coil spring 114 are made of stainless steel, preferably 304 stainless steel.

The core wire 116 extends along a longitudinal axis B-B from a core wire proximal portion 116A having a proximal end 116B to a core wire distal portion 116C having a distal end 116D. In this exemplary embodiment, the core wire 116 has a substantially constant first outer diameter 122 extending from the core wire proximal end 116B to a first transition indicated at 124. An exemplary first outer diameter ranges from about 0.004" to about 0.030".

A first tapered portion 116E extends distally and downwardly towards the longitudinal axis B-B from the first transition 124 to a second transition indicated at 126. A core wire intermediate portion 116F begins at the second transition 126. The intermediate portion 116F has a substantially constant second outer diameter 128, the second diameter 128 being less than the first diameter 122, and extends distally from the second transition 126 to a third transition indicated at 130. An exemplary second outer diameter 122 is of about 0.010±0.0005 inches. A second tapered portion 116G extends distally and downwardly towards the longitudinal axis B-B from the third transition 130 to a fourth transition indicated at 132 where the core wire distal portion 1160 begins. The distal portion 116C has a substantially constant third outer diameter 134, the third diameter 134 being less than the second outer diameter 128. An exemplary third outer diameter is about 0.0075 inches. The core wire distal portion 116C extends distally to the distal end 116D.

A distal atraumatic tip 136 is provided at the core wire distal end 116D. As previously described with respect to the atraumatic tip 22 in FIGS. 1 to 3, the tip 136 is preferably formed from the 304 stainless steel material comprising the outer sheath 118.

The outer sheath 118 is comprised of an outer sheath proximal portion 118A having a proximal end 118B. The outer sheath proximal portion 118B has a substantially constant thickness of from about 0.002" to about 0.008" and a substantially constant fourth outer diameter 138 extending distally to a fifth transition indicated at 140 so that the outer diameter 138 of the outer sheath 118 jacketing the inner core wire 116 ranges from about 0.008" to about 0.038" extending along the length of the proximal portion 118A. At the cross-section indicated at 140, the outer sheath 118 transitions to a tapered portion 118C that gradually reduces in cross-sectional diameter as it extends distally and downwardly toward the longitudinal axis B-B to terminate or taper out at the outer surface of the intermediate portion 116F of the core wire 116, proximal the atraumatic tip 136.

It will be readily apparent to those skilled in the art that while the core wire 116 comprising the drawn-filled tube 112 is shown having three constant diameter portions 116A, 116F and 116C, and two intermediate tapered portions 116E and 116G, that is for the sake of example only. Depending on the functional requirements of a particular guidewire design, there can be a greater or lesser number of constant diameter portions separated from each other by an intermediate tapered portion.

Further, while the tapered outer sheath portion 118C is shown terminating or tapering out at the intermediate constant diameter core wire portion 116F, that is exemplary. In another embodiment, the tapered outer sheath portion 118C tapers out at the distal constant diameter core wire portion 116C.

Moreover, while the first transition 124 of the core wire 116 and the fifth transition 140 of the sheath 118 are shown as coinciding in FIG. 4A, that is also by way of example. In other embodiments, the fifth transition 140 can occur either proximal or distal the first transition 124.

As is the case with the atraumatic tip 20 of the guidewire 10 shown in FIGS. 1 and 2, the atraumatic tip 136 for guidewire 110 can be a separate member that is secured to the core wire 116 at its distal end 116D or, preferably, the tip 136 is a portion of the outer sheath 118 supported on the core wire 116. The atraumatic tip has a beveled surface 136A that widens in cross-section from the core wire 116 to an intermediate cylindrical portion 136B having a diameter that is less than the second outer diameter 122 of the outer sheath proximal portion 118A. A sloped portion 136C extends distally and downwardly toward the core wire distal end 116D. If desired, the sloped portion 136C of tip can be curved to further enhance the atraumatic shape of the tip 136. In an alternate embodiment, the intermediate cylindrical portion 136B has an outer diameter that is the same as the fourth outer diameter 138 of the outer sheath portion 118B.

The proximal end 114A of the coil spring 114 is connected to the tapered portion 118C of the outer sheath 118. This connection is distal to the outer sheath proximal portion 118A having the substantially constant second outer diameter 122. The opposite distal end 114B of the coil spring 114 is connected to the atraumatic tip 136, preferably to the beveled surface 136A. The connections of the coil spring proximal end 114A to the tapered portion 118C of the outer sheath 118 and to the beveled portion 136A of the atraumatic tip 136 are made as a laser welder, a braze, or using a solder.

Figure 4B:
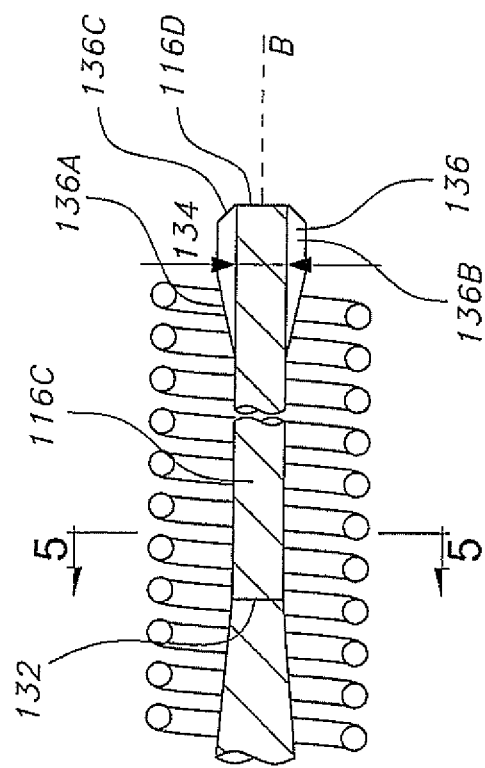
FIG. 4B is an enlarged view of an alternate embodiment of the indicated distal portion of the guidewire 110 shown in FIG. 4A.
Figure 5:
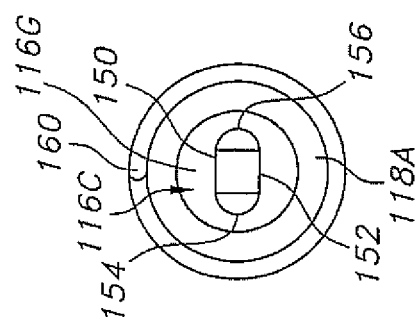
FIG. 5 is a cross-sectional view along line 5-5 of FIG. 4A.

FIG. 4B is an enlarged view of an alternate embodiment of the indicated distal portion of the guidewire 110 shown in FIG. 4A. FIG. 5 is a cress-sectional view taken along line 5-5 of FIG. 4A and illustrating that the distal portion 116C of the nitinol core wire 116 does not have the substantially constant third outer diameter 134. Instead, the distal portion 116C has a generally oval cross-section aligned perpendicular to the longitudinal axis B-B. In this embodiment, the distal portion 116C comprises opposed substantially parallel planar surfaces 150 and 152 extending from the fourth transition indicated at 132 to the atraumatic tip 136. The planar surfaces 150, 152 are joined to each ether by opposed radiused or curved surfaces 154 and 156. This shape for the distal portion 116C of the nitinol core wire 116 can be set using a fluidized bath or air furnace, and the like, and enhances the stiffness of the nitinol core wire 116 adjacent to the atraumatic tip 136.

FIG. 5 further illustrates that a polymeric coating 160 is provided on the proximal and tapered portions 118A and 118C of the outer sheath 118. While not shown in the drawing, the polymer coating 160 also preferably covers the coil spring 114. Polyurethane is a preferred material for the coating 160.

Figure 6:
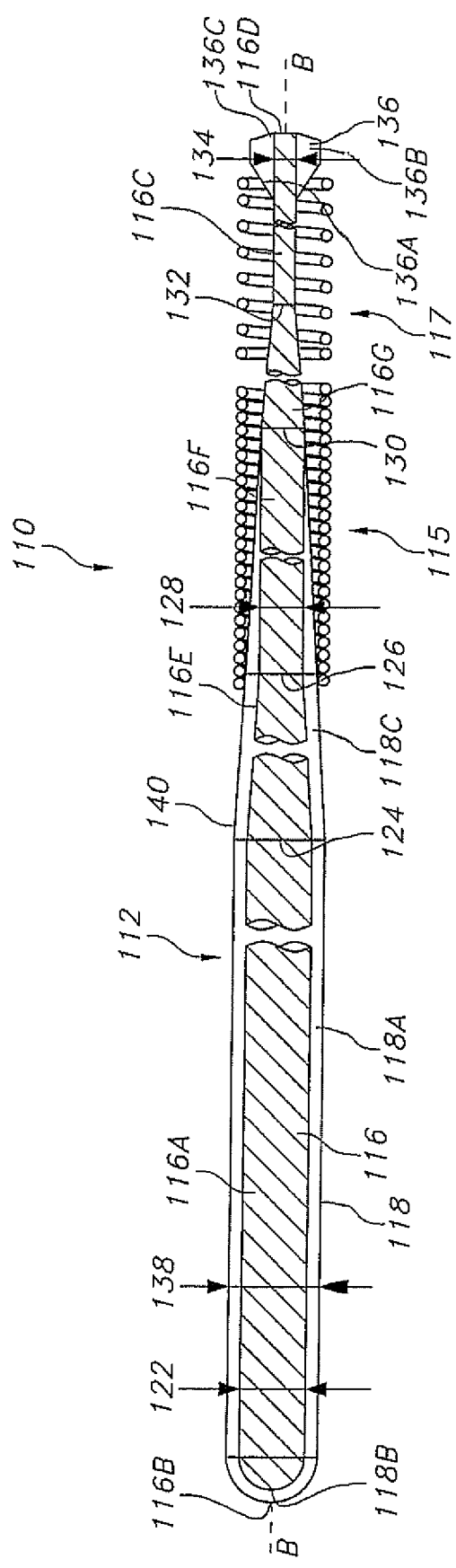
FIG. 6 is an elevational of then guidewire 110 shown in FIG. 4A, but with the spring 114 having been replaced by a proximal non-radiopaque coil spring 115 connected to a distal radiopaque spring 117 according to the present invention.

FIG. 6 is an elevational view of the guidewire 110 illustrated in FIGS. 4A and 4B, but with the stainless steel coil spring 114 replaced with two coil springs 115 and 117. Preferably, the proximal coil spring 115 is of a non-radiopaque material, for example, stainless steel, and the distal coil spring 117 is of a radiopaque material, for example titanium. At their respective distal and proximal ends, the coil springs 115, 117 either overlap each other, are interwound or soldered together. Further, the connection between the coil springs 115, 117 is either supported by a solder or like material that also contacts the core wire 116, or the connection between the springs is unsupported. In any event, the radiopaque coil spring 117 helps a physician visualize the distal portion of the guidewire 110 as it is moved through the vasculature of a patient.

Thus, various embodiments of guidewires made from a drawn-filled tube comprising a stainless steel cuter sheath jacketing a nitinol core wire are described. The proximal end of the guidewire with the nitinol/stainless steel drawn-filled tube composite is stiffer than the nitinol distal portion due to the relative stiffness of stainless steel. The stiffness of the guidewire can be tailored by changing the ratio of the thickness of the stainless steel outer sheath to that of the nitinol core wire. This thickness ratio can be controlled by grinding or cold working when the drawn-filled tube is manufactured.

It is appreciated that various modifications to the present inventive concepts described herein may be apparent to those of ordinary skill in the art without departing from the scope of the present invention as defined by the herein appended claims.

What is claimed is:

1. A method for manufacturing a guidewire, comprising the steps of:
   a) providing a drawn-filled tube extending along a longitudinal axis and comprising an outer sheath contacting an inner core wire, wherein the outer sheath extends from an outer sheath proximal portion having an outer sheath proximal end to an outer sheath distal portion having an outer sheath distal end, and wherein the inner core wire extends from a core wire proximal portion having a core wire proximal end to a core wire distal portion having an exposed core wire distal end that is coincident with the outer sheath distal end; and
   b) machining the drawn-filled tube so that:
      i) the outer sheath proximal portion contacting the core wire proximal portion extends to at least one outer sheath tapered portion that extends distally and downwardly toward the longitudinal axis to taper out at the core wire distal end; and
      ii) an atraumatic tip portion of the outer sheath is supported on and contacts the core wire distal portion with the exposed core wire distal end remaining exposed and being coincident with a distal end of the atraumatic tip.

2. The method of claim 1, including machining the atraumatic tip portion to have an atraumatic tip distal sloped portion that extends distally and downwardly toward the longitudincla axis so that the distal end of the atraumatic tip portion meets and is coincident with the exposed core wire distal end.

3. The method of claim 2, including machining the atraumatic tip distal sloped portion to have a curved shape.

4. The method of claim 1, including providing the outer sheath of the drawn-filled tube comprising stainless steel and the inner core wire comprising a superelastic nickel-titanium alloy.

5. The method of claim 2, including machining the atraumatic tip portion of the outer sheath to comprise an atraumatic tip cylindrically-shaped portion residing intermediate an atraumatic tip proximal beveled portion and the atraumatic tip distal sloped portion, wherein the atraumatic tip proximal beveled portion tapers from the atraumatic tip cylindrically-shaped portion downwardly and proximally along the longitudinal axis to the core wire.

6. The method of claim 1, including providing the drawn-filled tube with the the core wire proximal portion having a substantially constant first outer diameter and at least one core wire tapered portion that tapers downwardly and distally from the core wire proximal portion toward the longitudinal axis to the core wire distal portion having a substantially constant second outer diameter less than the first outer diameter.

7. The method of claim 1, including providing the drawn-filled tube with the core wire proximal portion having a substantially constant first outer diameter extending to a core wire first tapered portion tapering downwardly and distally from the core wire proximal portion toward the lognitudinal axis to a core wire intermediate portion having a substantially constant second outer diameter that is less than the first outer diameter, and with the core wire intermediate portion extending to a core wire second tapered portion tapering downwardly and distally from the core wire intermediate portion toward the longitudinal axis to the core wire distal portion having a substantially constant third outer diameter that is less than the second outer diameter.

8. The method of claim 1, including machining the atraumatic tip portion of the outer sheath having a tip outer diameter that is substantially the same as or less than an outer diameter of the outer sheath proximal portion.

9. The method of claim 1, including providing the core wire distal portion having an oval cross-section perpendicular to the longitudinal axis, the oval cross-section residing between where the outer sheath tapered portion tapers out at the core wire and the atraumatic tip portion of the outer sheath.

10. The method of claim 9, including:
a) providing the core wire comprising a superelastic nickel-titanium alloy; and
b) subjecting the core wire distal portion to an annealing step where the superelastic nickel-titanium alloy is heated to a temperature ranging from 300° C. to 600° C. for a period ranging from five minutes to two hours, thereby shaping the core wire distal portion into a curved configuration.

11. The method of claim 1, including machining the drawn-filled tube using a grinding cam.

12. The method of claim 1, including providing the core wire as a solid member that does not have a lumen.

13. A method for manufacturing a guidewire, comprising the steps of:
a) providing a drawn-filled tube extending along a longitudinal axis and comprising an outer sheath contacting an inner core wire, wherein the outer sheath extends from an outer sheath proximal portion having an outer sheath proximal end to an outer sheath distal portion having an outer sheath distal end, and wherein the inner core wire extends from a core wire proximal portion having a core wire proximal end to a core wire distal portion having an exposed core wire distal end that is coincident with the outer sheath distal end;
b) machining the drawn-filled tube so that:
  i) the outer sheath proximal portion contacting the core wire proximal portion extends to an outer sheath tapered portion that extends distally and downwardly toward the longitudinal axis to taper out at the core wire at a location proximal the core wire distal end; and
  ii) an atraumatic tip portion of the outer sheath is supported on and contacts the core wire distal portion, wherein the atraumatic tip portion has a distal sloped portion that extends distally and downwardly toward the longitudinal axis so that a distal end of the atraumatic tip portion meets and is coincident with the exposed core wire distal end; and
c) providing a first coil spring of a non-radiopaque material extending from a first coil spring proximal portion to a first coil spring distal end, and a second coil spring of a radiopaque material extending from a second coil spring proximal portion to a second coil spring distal portion; and
d) connecting the first coil spring proximal portion to the outer sheath proximal portion, connecting the second coil spring distal portion to the atraumatic tip portion of the outer sheath, and connecting the first coil spring distal end to the second coil spring proximal portion.

14. The method of claim 13, including providing the atraumatic tip portion of the outer sheath having an atraumatic tip proximal beveled portion that extends distally from the core wire and widens outwardly in cross-section to an atraumatic tip intermediate cylindrically-shaped portion meeting the atraumatic tip distal sloped portion that extends distally and downwardly toward the longitudinal axis so that the distal end of the atraumatic tip portion meets and is coincident with the exposed core wire distal end.

15. The method of claim 14, including connecting the first coil spring proximal portion to the outer sheath tapered portion, and connecting the second coil spring distal portion to the atraumatic tip proximal beveled portion of the atraumatic tip portion of the outer sheath.

16. The method of claim 13, including providing the core wire comprising a superelastic nickel-titanium alloy, and subjecting the core wire distal portion to an annealing step where the superelastic nickel-titanium alloy is heated to a temperature ranging from 300° C. to 600° C. for a period ranging from five minutes to two hours, thereby shaping the core wire distal portion into a curved configuration.

17. A method for manufacturing a guidewire, comprising the steps of:
a) providing a drawn-filled tube extending along a longitudinal axis and comprising an outer sheath comprising stainless steel contacting an inner core wire comprising a superelastic nickel-titanium alloy, wherein the outer sheath extends from an outer sheath proximal portion having an outer sheath proximal end to an outer sheath distal portion having an outer sheath distal end, and wherein the inner core wire extends from a core wire proximal portion having a core wire proximal end to a core wire distal portion having an exposed core wire distal end that is coincident with the outer sheath distal end;
b) machining the drawn-filled tube so that:
  i) the outer sheath proximal portion contacting the core wire proximal portion extends to an outer sheath tapered portion that extends distally and downwardly toward the longitudinal axis to taper out at the core wire at a location proximal the core wire distal end; and
  ii) an atraumatic tip portion of the outer sheath is supported on and contacts the core wire distal portion, wherein the atraumatic tip portion has an atraumatic tip distal sloped portion that extends distally and downwardly toward the longitudinal axis so that a distal end of the atraumatic tip portion meets and is coincident with the exposed core wire distal end; and
c) providing at least one coil spring extending from a coil spring proximal portion to a coil spring distal end; and d) connecting the coil spring proximal portion to the outer sheath proximal portion and connecting the coil spring distal end to the atraumatic tip portion of the outer sheath.

18. The method of claim 17, including subjecting the core wire distal portion to an annealing step where the superelastic nickel-titanium alloy is heated to a temperature ranging from 300° C. to 600° C. for a period ranging from five minutes to two hours, thereby shaping the core wire distal portion into a curved configuration.

19. The method of claim 1, including:
a) providing at least one coil spring extending from a coil spring proximal portion to a coil spring distal portion; and
b) connecting the coil spring proximal portion to the outer sheath tapered portion and connecting the coil spring distal portion to the atraumatic tip portion of the outer sheath.

20. The method of claim 19, including:
a) providing the at least one coil spring comprising:
  i) a first coil spring extending from a first coil spring proximal portion to a first coil spring distal end; and
  ii) a second coil spring extending from a second coil spring proximal portion to a second coil spring distal end;
b) connecting the first coil spring proximal portion to the taper of the outer sheath proximal portion;
c) connecting the second coil spring distal end to the atraumatic tip portion of the outer sheath; and
d) connecting the first coil spring distal end to the second coil spring proximal portion.

21. The method of claim 20, including either supporting the connection between the first and second coil spring distal portion and second coil spring proximal portion using solder contacting the core wire, or the connection between the first coil spring distal portion and second coil spring proximal portion is unsupported.

22. The method of claim 19, including providing the at least one coil spring comprising a proximal coil spring of a non-radiopaque material connected to a distal coil spring of a radiopaque material.

23. The method of claim 19, including coating polyurethane on at least one of the outer sheath proximal portion and the at least one coil spring.

* * * * *